US009962086B2

(12) United States Patent
Dabbah et al.

(10) Patent No.: US 9,962,086 B2
(45) Date of Patent: May 8, 2018

(54) MEDICAL IMAGE DATA PROCESSING APPARATUS AND METHOD FOR DETERMINING THE PRESENCE OF AN ABNORMALITY

(71) Applicant: Toshiba Medical Systems Corporation, Otawara-shi (JP)

(72) Inventors: Mohammad Dabbah, Edinburgh (GB); Keith Goatman, Edinburgh (GB); Ian Poole, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days. days.

(21) Appl. No.: 14/674,543

(22) Filed: Mar. 31, 2015

(65) Prior Publication Data
US 2016/0292864 A1 Oct. 6, 2016

(51) Int. Cl.
*G06K 9/00* (2006.01)
*A61B 5/00* (2006.01)
(Continued)

(52) U.S. Cl.
CPC .............. *A61B 5/004* (2013.01); *A61B 6/461* (2013.01); *A61B 6/486* (2013.01); *A61B 6/50* (2013.01);
(Continued)

(58) Field of Classification Search
None
See application file for complete search history.

(56) References Cited

U.S. PATENT DOCUMENTS 7,903,849 B2 * 3/2011 Kimura ............... G06T 7/30
378/21
8,724,850 B1 * 5/2014 Hanson ............... G06K 9/4642
345/474
(Continued)

FOREIGN PATENT DOCUMENTS

JP          2014-64733 A      4/2014
WO     WO 2014/162911 A1   10/2014

OTHER PUBLICATIONS

Gorbunova et al ("Early Detection of Emphysema Progression", 2010).*

(Continued)

*Primary Examiner* — Avinash Yentrapati
(74) *Attorney, Agent, or Firm* — Oblon, McClelland, Maier & Neustadt, L.L.P.

(57) ABSTRACT

A medical imaging data processing apparatus comprises a receiving unit configured to receive first medical imaging data that represents a region of a subject at a first time, and second medical imaging data that represents the region of the subject at a second, later time, a registration unit configured to perform a registration procedure to obtain registration data representative of a registration between the first medical imaging data and the second medical imaging data, an evaluation unit configured to process the registration data to determine, for each of a plurality of positions in the region, a value of a registration measure, the registration measure representing at least one feature of the registration as a function of position, wherein the evaluation unit is configured to, for at least some of the plurality of positions in the region, determine whether an abnormality is present by comparing the value of the registration measure to a statistical atlas.

19 Claims, 6 Drawing Sheets

(51) Int. Cl.
  *G06T 11/00* (2006.01)
  *A61B 8/08* (2006.01)
  *A61B 6/00* (2006.01)
  *G06T 7/00* (2017.01)
  *G06T 7/33* (2017.01)

(52) U.S. Cl.
  CPC .......... *A61B 6/5217* (2013.01); *A61B 6/5235* (2013.01); *A61B 8/08* (2013.01); *G06T 7/0014* (2013.01); *G06T 7/337* (2017.01); *G06T 11/001* (2013.01); *A61B 6/541* (2013.01); *G06T 2207/10016* (2013.01); *G06T 2207/10081* (2013.01); *G06T 2207/30061* (2013.01)

(56) References Cited

U.S. PATENT DOCUMENTS

| | | | |
|---|---|---|---|
| 2001/0048757 A1* | 12/2001 | Oosawa | G06T 7/32 382/130 |
| 2002/0169730 A1* | 11/2002 | Lazaridis | G06F 19/20 706/20 |
| 2002/0181754 A1* | 12/2002 | Masumoto | G06T 7/11 382/131 |
| 2005/0074151 A1* | 4/2005 | Chen | A61B 1/00009 382/128 |
| 2006/0233430 A1* | 10/2006 | Kimura | G06T 7/30 382/128 |
| 2007/0019846 A1* | 1/2007 | Bullitt | G06T 7/0014 382/128 |
| 2007/0081707 A1* | 4/2007 | Sirohey | G06F 19/3431 382/128 |
| 2008/0019580 A1* | 1/2008 | Ohyu | G06K 9/3216 382/130 |
| 2008/0175464 A1* | 7/2008 | Brett | G06T 7/0012 382/131 |
| 2008/0200840 A1* | 8/2008 | Tamez-Pena | A61B 5/055 600/587 |
| 2008/0292194 A1* | 11/2008 | Schmidt | G06T 7/0012 382/217 |
| 2010/0324409 A1* | 12/2010 | Assmann | A61B 5/055 600/410 |
| 2011/0019889 A1* | 1/2011 | Gering | A61B 6/032 382/131 |
| 2011/0058721 A1* | 3/2011 | Zhang | A61B 5/08 382/131 |
| 2011/0158491 A1* | 6/2011 | Markova | G06T 3/0081 382/128 |
| 2011/0286652 A1* | 11/2011 | Kabus | A61B 6/5235 382/131 |
| 2012/0070044 A1* | 3/2012 | Avinash | G06K 9/3233 382/128 |
| 2013/0004044 A1* | 1/2013 | Ross | G06T 7/0016 382/131 |
| 2013/0044927 A1* | 2/2013 | Poole | G06T 7/0014 382/131 |
| 2013/0172727 A1* | 7/2013 | Mori | A61B 5/055 600/407 |
| 2013/0194266 A1* | 8/2013 | Forster | A61B 6/5229 345/424 |
| 2013/0202170 A1* | 8/2013 | Blezek | G06K 9/00201 382/131 |
| 2015/0161782 A1* | 6/2015 | Mohr | G06K 9/627 382/128 |
| 2015/0294445 A1* | 10/2015 | Sakaue | A61B 6/469 382/131 |
| 2016/0022240 A1* | 1/2016 | Yamagata | A61B 6/5217 382/131 |
| 2016/0180525 A1* | 6/2016 | Reynolds | G06T 7/11 382/131 |

OTHER PUBLICATIONS

Craig J. Galban, et al., "Computed tomography-based biomarker provides unique signature for diagnosis of COPD phenotypes and disease progression" Nature Medicine, vol. 18, No. 11, Nov. 2012, pp. 1711-1716.

Jim Piper, et al., "Objective Evaluation of the Correction by Non-Rigid Registration of Abdominal Organ Motion in Low-Dose 4D Dynamic Contrast-Enhanced CT" Physics in Medicine and Biology, 2012, pp. 1-17.

William R. Crum, et al., "Information Theoretic Similarity Measures in Non-Rigid Registration" Proceedings of IPMI, 2003, 10 Pages.

Mattias P. Heinrich, et al., "MRF-Based Deformable Registration and Ventilation Estimation of Lung CT" IEEE Transactions on Medical Imaging, vol. 32, No. 7, Jul. 2013, pp. 1239-1248.

Eric W. Weisstein. "Jacobian" MathWorld—A Wolfram Web Resource: http://mathworld.wolfram.com/Jacobian.html, Mar. 27, 2015, 2 Pages.

* cited by examiner

MEDICAL IMAGE DATA PROCESSING APPARATUS AND METHOD FOR DETERMINING THE PRESENCE OF AN ABNORMALITY

FIELD

The present invention relates to the determination of abnormalities in medical imaging data, for example abnormalities in the lungs such as abnormalities that may arise from chronic obstructive pulmonary disease (COPD).

BACKGROUND

A variety of medical imaging modalities, for example computerized tomography (CT), magnetic resonance imaging (MRI), positron emission tomography (PET) and ultrasound, have become well-known techniques for obtaining medical imaging data representative of a patient or other subject for diagnostic or other purposes.

It is known to obtain multiple medical imaging data sets of the same patient or other subject by performing measurements at different times, under different conditions or using different modalities. Such multiple medical imaging data sets often have different co-ordinate systems, such that the same anatomical feature of the subject will appear at positions having different co-ordinates in the different medical imaging data sets (for example, in a simple case, due to the patient or other subject having a different relative position within the scanner when the different imaging data sets were obtained).

It is known to register different medical imaging data sets, for example different medical imaging data sets for the same patient or other subject obtained at different times, to obtain registration data that comprises or represents a transformation of co-ordinates for one or both of the medical imaging data sets. By transforming the co-ordinates of one or both medical imaging data sets it can be provided that the medical imaging data sets are aligned such that the same anatomical features from the medical imaging data sets appear at substantially the same, or corresponding, positions in a common co-ordinate system.

It is known to perform registrations manually or automatically using known analysis techniques. Different types of registration transformation may be used, for example (in order of increasing degrees of freedom) rigid body, affine, or non-rigid.

A rigid body registration in this context may comprise a registration in which the co-ordinates of data points in one data set are subject to rotation and/or translation in order to register the data set to another data set. An affine registration in this context may comprise a registration in which the coordinates of data points in one dataset are subject to rotation, and/or translation, and/or scaling and/or shearing in order to register the dataset to another dataset. Thus, a rigid registration may be considered to be a particular type of affine registration.

Non-rigid registrations can provide different displacements for each voxel of the data set to be registered and can, for example, use non-linear transformations, in which the coordinates of data points in one dataset are subject to flexible deformations in order to register the data set to another data set. Non-linear transformations may in some cases be defined using vector fields such as warp fields, or other fields or functions, such as B-splines, defining an individual displacement for each voxel in a three-dimensional data set.

Chronic obstructive pulmonary disease (COPD) was the fourth leading cause of death in 2011, responsible for an estimated 3 million deaths worldwide. Currently, diagnosis is made primarily using non-imaging methods, with severity rated using a single measure for both lungs known as the Global Initiative for Chronic Obstructive Lung Disease (GOLD) severity score. Although there is currently no cure for COPD, appropriate early treatment can slow progression and improve the patient's quality of life. COPD can include one or more of a variety symptoms and conditions, for example emphysema, bronchitis, and functional small airways disease (fSAD).

It has been suggested to use imaging methods to diagnose or monitor COPD. In particular, it has been suggested to diagnose COPD based on two lung CT scans: one acquired at full inspiration, the other at full expiration. Inspiration scan voxels with CT intensity values less than a first threshold are identified as representing emphysema tissue. Expiration scan voxels with CT intensity values less than a second threshold are considered to indicate gas trapping. Using those thresholds and a parametric response map that represents the combinations of CT intensity values from both the expiration and inspiration scans, normal tissue, emphysema, and a category of functional small airways disease (fSAD) for tissue where there is gas trapping but not emphysema, are determined based on the CT intensity values. The known method is based on comparisons of the CT intensity values to thresholds.

BRIEF DESCRIPTION OF THE DRAWINGS

Embodiments are now described, by way of non-limiting example, and are illustrated in the following figures, in which.

DETAILED DESCRIPTION

Certain embodiments provide a medical imaging data processing apparatus comprising a receiving unit configured to receive first medical imaging data that represents a region of a subject at a first time, and second medical imaging data that represents the region of the subject at a second, later time; a registration unit configured to perform a registration procedure to obtain a registration between the first medical imaging data and the second medical imaging data; an evaluation unit configured to, for at least some of the plurality of positions in the region, determine whether an abnormality is present by comparing the value of a parameter of the registration, or of the registered first or second medical imaging data, to a statistical atlas.

Certain embodiments provide a medical imaging data processing method comprising: —receiving first medical imaging data that represents a region of a subject at a first time, and second medical imaging data that represents the region of the subject at a second, later time; performing a registration procedure to obtain a registration between the first medical imaging data and the second medical imaging data; and for at least some of the plurality of positions in the region, determining whether an abnormality is present by comparing the value of a parameter of the registration, or of the registered first or second medical imaging data, to a statistical atlas.

Figure 1:
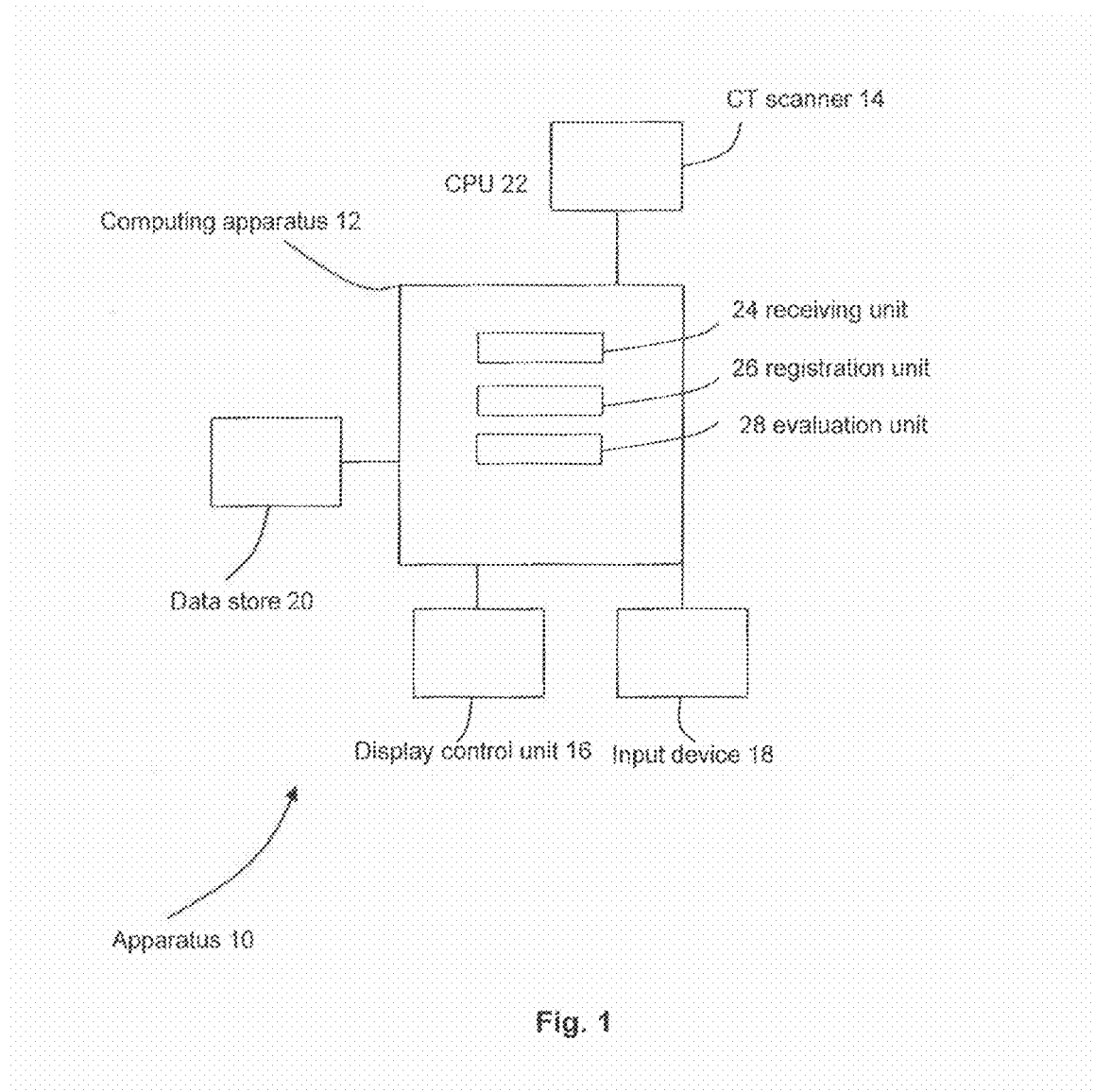
FIG. 1 is a schematic illustration of an imaging data processing system according to an embodiment.

An imaging data processing apparatus 10 according to an embodiment is illustrated schematically in FIG. 1.

The imaging data processing apparatus 10 comprises a computing apparatus 12, in this case a personal computer (PC) or workstation, that is connected to a CT scanner 14, a display control unit 16 including or associated with a display screen, and an input device or devices 18, such as a computer keyboard and mouse. In the present embodiment, imaging data is obtained by the CT scanner 14 and stored in data store 20. In other embodiments, imaging data may be loaded from a remote data store or other memory. Any suitable CT scanner may be used.

Computing apparatus 12 provides a processing resource for receiving and processing medical imaging data. Computing apparatus 12 includes a receiving unit 24 for receiving medical imaging data from the CT scanner 14, from the data store 20 or from a remote data store or other memory. Computing apparatus 12 also includes a registration unit 26 for performing a registration process to obtain registration data representative of registrations between sets of the medical imaging data. Computing apparatus 12 further includes an evaluation unit 28, which is configured to process the registration data to determine values of registration measures obtained in respect of the registrations. The evaluation unit 28 is further configured to compare the values of the registration measures to a statistical atlas and to determine a measure of abnormality based on the comparison, as is described in more detail below.

In the present embodiment, the receiving unit 24, the registration unit 26, and the evaluation unit 28 are each implemented in computing apparatus 12 by means of a computer program having computer-readable instructions that are executable by a central processing unit (CPU) of the computing apparatus to perform the method of the embodiment. However, in other embodiments, the various units may be implemented as hardware, software or any suitable combination or hardware and software. In some embodiments, the units may be implemented, for example, as one or more ASICs (application specific integrated circuits) or FPGAs (field programmable gate arrays) or other dedicated circuitry.

The computing apparatus 12 also includes a hard drive and other components of a PC including RAM, ROM, a data bus, an operating system including various device drivers, and hardware devices including a graphics card. Such components are not shown in FIG. 1 for clarity.

It is a feature of the embodiment of FIG. 1 that it is configured to perform a process that determines a measure of abnormality for a plurality of voxels obtained from CT measurements on a patient's lung or lungs, based on comparison of values of a registration measure to a statistical atlas. The process of the embodiment is illustrated in overview in the flowchart of FIG. 2.

At stage 40, the receiving unit 24 receives a pair of medical imaging data sets, comprising a first set of medical imaging data and a second set of imaging data that were obtained from scans performed by the CT scanner 14 on the same region of a subject but at different times. In this case, the first set of medical imaging data is CT scan data representative of the chest cavity region of a patient and including CT data representing the patient's lungs in an inhalation state (for example, when the patient was in the process of inhaling or had substantially fully inhaled), and the second set of medical imaging data is CT scan data representative of the chest cavity region of the patient and including CT data representing the patient's lungs during a subsequent exhalation state (for example, when the patient was in the process of exhaling or had substantially fully exhaled) immediately following the inhalation state that is the subject of the first medical imaging data set. The first medical imaging data set may be referred to as the inspire volume, and the second medical imaging data set may be referred to as the expire volume in this case.

Both the first and second medical imaging data sets in this case comprise volumetric data comprising a three-dimensional array of voxels, each voxel having a position value representative of the position the voxel corresponds to in the scanned volume, and an intensity value representative of attenuation of X-ray radiation of the CT scan at that position. The intensity value representative of attenuation is usually measured in Hounsfield units (HU).

At stage 42, the first and second medical image data sets are registered and a scalar field comprising registration measure values determined based on the registration is obtained. That process, at stage 42, of registering the datasets and obtaining the scalar field comprises several stages. Details of the process of stage 42 are illustrated in overview in the flowchart of FIG. 3, and comprises stages 50 to 62.

Figure 3:
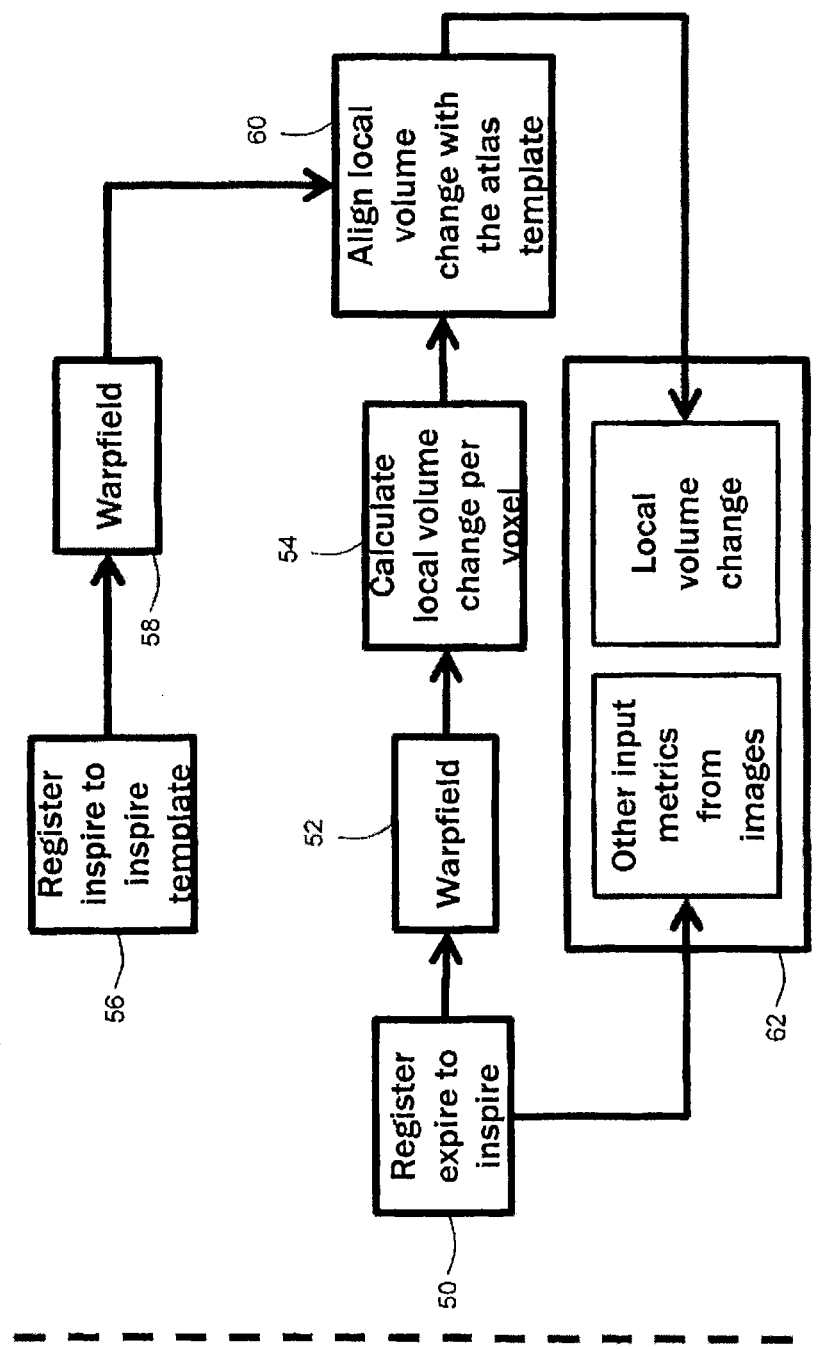
FIG. 3 is a flow chart representing in more detail certain stages of the process of FIG. 2.

At the first stage 50 of FIG. 3, the registration unit 26 registers the first set of imaging data with the second set of imaging data using a non-rigid registration procedure. Any suitable non-rigid registration procedure may be used. In the present embodiment, the non-rigid registration procedure is similar to that reported in Piper, J et al, Objective evaluation of the correction by non-rigid registration of abdominal organ motion in low-dose 4D dynamic contrast-enhanced CT, Physics in Medicine and Biology 57(6), 1701-1715 (2012). A global non-rigid registration procedure is performed, for example using Mutual Information as a similarity measure, and a deformation field is computed using the Crum-Hill-Hawkes scheme (William R. Crum, Derek L. G. Hill, David J. Hawkes. Information Theoretic Similarity Measures in Non-rigid Registration, Proceedings of IPMI '2003, pp. 378-387). In the present embodiment, the deformation field is a dense vector field, in which an individual displacement vector is defined for each voxel. Any other suitable registration procedure may be used in alternative embodiments. For example any suitable registration algorithm, such as a non-rigid registration algorithm, that is able to distinguish differential motion at different locations within the medical imaging data sets may be used. In some embodiments, a discrete optimization with dense displacement sampling (DEEDS) algorithm may be used. An example of a DEEDS algorithm is described in "MRF-Based Deformable Registration and Ventilation Estimation of Lung CT", Mattias P. Heinrich, M. Jenkinson, M. Brady and J. A. Schnabel. IEEE Transactions on Medical Imaging 2013, Volume 32, Issue 7, July 2013, Pages 1239-1248.

The output of the registration procedure performed by the registration unit 26 at stage 50 is provided at stage 52 as a set of registration data in the form of a warp field that represents an offset in co-ordinates for a plurality of locations in the second imaging data set that align those locations with corresponding locations in the first imaging data set. Thus, for example, if the registration were perfect and if the co-ordinates of each voxel in the second imaging data set were to be transformed in accordance with the registration data then corresponding anatomical features (for example lung features or other organ features) would be represented at substantially the same positions in the first imaging data set and in the transformed second imaging data set.

In the present embodiment, the registration data comprise a warp field that comprises, for each voxel of the second imaging data set, a respective vector that comprises a direction and magnitude of displacement of that voxel required to align it with a corresponding voxel of the first imaging data set. Any suitable type of registration data may be used in other embodiments, for example any suitable vector field or any other suitable field or function, or any other suitable data that represents a registration or transformation between co-ordinates.

At the next stage, 54, the evaluation unit 28 calculates a log of a Jacobian of the registration data, in this case the registration warp field, for each voxel position. The Jacobian in this embodiment for each voxel position represents the partial derivative of the warp field at the voxel position with respect to each spatial dimension. Jacobians are described for example in http://mathworld.wolfram.com/Jacobian.html.

The log of the Jacobian is representative, for each voxel, of the local volume change between inhalation and exhalation (also referred to as inspiration and expiration), and can be referred to as a registration measure. The values of the registration measure for different positions in the co-ordinate space of the registered data sets make up a scalar field. In the present embodiment, a respective value of the registration measure (in this case represented by the log of the Jacobian) is determined for each voxel.

As well as the registration of the first medical image data set and the second medical image data set at stage 50, the registration unit 26 also, at stage 56, registers the first medical image data set (also referred to as the inspire volume or inspire) to a template data set that forms part of, or is associated with, a statistical atlas. The registration in this embodiment is obtained using a non-rigid registration procedure such as described in relation to stage 50, although any suitable registration procedure can be used in alternative embodiments. The output of the registration of the first medical image data set and the template data set at stage 56 is a warp field that comprises, for each voxel of the first medical imaging data set, a respective vector that comprises a direction and magnitude of displacement of that voxel required to align it with a corresponding voxel of the template data set.

The template data set in this case comprises a set of voxels, each voxel representing an average intensity value obtained by averaging intensity values for that voxel position obtained from a plurality of reference datasets. The reference data sets in this embodiment are obtained from measurements of a plurality of reference subjects (e.g. patients having normal anatomy) during an inhalation phase (also referred to as an inspiration phase) and the template data set can be referred to as an inspire template.

The statistical atlas data set, including the template data set, in this embodiment is a pre-calculated statistical atlas data set stored in data store 20. However the statistical atlas data set may also be calculated as part of the process in alternative embodiments. A process for determining the statistical atlas data set according to an embodiment is described in more detail below in relation to FIG. 6.

Returning to the process of FIG. 3, the registration unit 26 uses the warp field obtained at stage 58 from the registration of the first medical image data set to the template data set, to transform the co-ordinates of the scalar field data (the log Jacobian values representative of local volume change in this case) obtained at stage 54 into the co-ordinate space of the statistical atlas and template data set.

The scalar field data is transformed in accordance with the warp field obtained at stage 58, such that, for each voxel of the first medical image data set, the scalar field value (e.g. log Jacobian value) representative of the local volume change between inhalation and exhalation at that voxel position determined from the first and medical image data sets for the patient is aligned with corresponding anatomical position in the statistical atlas and template data set. Thus, corresponding anatomical features may be represented at the same position in a common co-ordinate space in both the scalar field data and in the statistical atlas and template data set.

At the next stage the transformed scalar field data may be supplemented with further data, for example other metrics obtained from or associated with the first and/or second medical imaging data. In this embodiment, the further data comprises the voxel intensity values of the first medical image data set. These are combined with the log Jacobian values that have been determined such that each voxel, or voxel position, of the scalar field data obtained at the end of stage 62 comprises a log Jacobian value (representative of local volume change between inhalation and exhalation at that voxel position) and CT intensity value obtained during the inhalation phase for that voxel position. Thus, in this embodiment, the scalar field data at the end of stage 62 is two-dimensional scalar field data. The process of FIG. 3 generates the scalar field data from the intensity values and non-rigid registration warp field of the CT dataset inspiration/expiration pair for the patient (the first and second medical image datasets).

Figure 2:
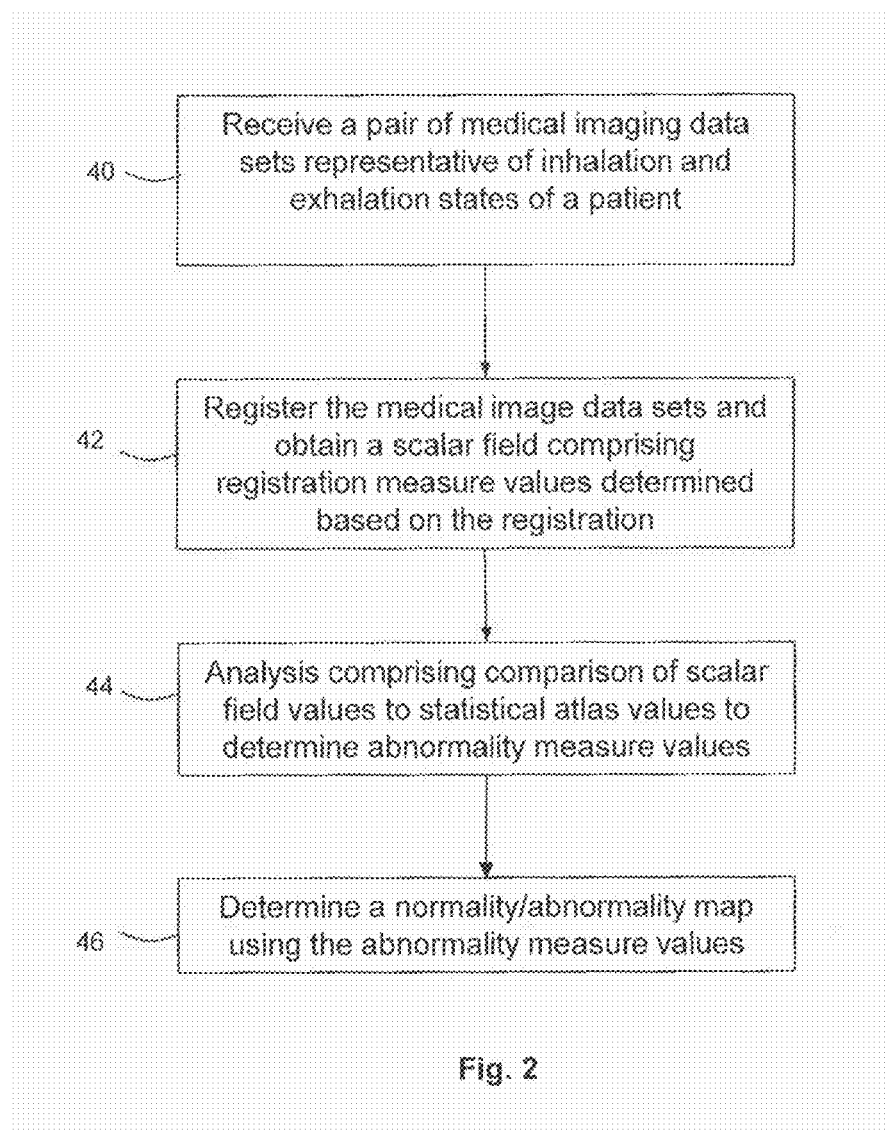
FIG. 2 is a flow chart representing in overview a process for determining abnormalities in medical image data sets according to an embodiment.

At the end of stage 62 of FIG. 3, the process returns to stage 44 of the main process of FIG. 2. At stage 44, the evaluation unit performs an analysis that comprises comparing the scalar field data values obtained for the patient at stage 62 to statistical atlas values to determine values of an abnormality measure for the patient.

Considering the process of stage 44 in more detail, the statistical atlas in this embodiment comprises or represents, for each voxel position, a distribution of values of the registration measure (in this case, log Jacobian values) for that voxel position that were obtained in respect of registration of a plurality of pairs of reference medical imaging data sets obtained from a plurality of reference patients or other subjects. Each of the plurality of pairs comprises a medical imaging data set obtained during an inhalation phase and a medical imaging data set obtained during an exhalation phase, and for each voxel position, a log Jacobian value is calculated for each of the pairs of data sets, thus giving a distribution of log Jacobian values for each voxel position. Of the pairs of reference medical imaging data sets used to obtain the statistical atlas, the reference medical imaging data sets obtained during the inhalation phases are also used to obtain the template medical imaging data set that is used in the registration at stage 56.

In the present embodiment, for each voxel position the comparison to the statistical atlas comprises determining a statistical distance of the registration measure value (in this case the log Jacobian value) that is representative of where the registration measure value falls on the distribution of registration measure values for that voxel position. In this case the statistical distance that is determined is the number of standard deviations from the center of the distribution. The statistical distance that is determined can be taken as being an abnormality measure. The further from the center of the distribution that a registration measure value falls, the more likely it is to be considered abnormal.

In some embodiments, the values of the abnormality measure that are determined are compared to a threshold, and for example are classified as being either normal or abnormal in dependence on the comparison.

The registration measure values in this embodiment are representative of local volume change (represented by the log Jacobian values) and so the expected distribution of values encountered for normal patients (e.g. the reference subjects used to obtain the statistical atlas) for a particular voxel position will be different depending on the anatomical feature represented by that voxel. For instance, the local volume change between inhalation and exhalation phases for voxel positions representative of bone will be very small, effectively zero, in the absence of misregistrations. Thus, the distribution of registration measure values for such voxel positions in the statistical atlas would be expected to be narrow. In contrast, for voxel positions representative of lung tissue the distribution of registration measure values in the statistical atlas may be wide, as local volume change between inhalation and exhalation phases can be expected to vary significantly between reference patients, for example dependent on variations of lung capacity, structure and function between patients.

The use of a statistical distance, for example number of standard deviations, as the measure of abnormality can take into account the variability of the distribution width at different voxel positions, in contrast to the use solely of fixed thresholds for all voxel positions. Any suitable measure can be used as the measure of abnormality, for example the measure of statistical distance, in alternative embodiments. For instance, one or more of a z-score, a Mahalanobis distance or a number of standard deviations may be used in embodiments. When using a single metric (local volume change) the measure may, for example, be a z-score but this can be expanded when using additional metrics (for example, the original HU values) using for example the Mahalanobis distance.

At the end of stage 44 of the embodiment of FIG. 3, an abnormality measure value is determined for each voxel position. In this case, the abnormality measure value for each voxel position represents the number of standard deviations of the registration measure value (the log Jacobian, representative of local volume change, in this case) for that voxel away from the center of the distribution of registration measure values of the statistical atlas for that voxel.

At the next stage 46, a normality or abnormality map may be generated that represents graphically for each voxel position the value of the abnormality measure for that voxel position. For example, visual effects that depend on the values of abnormality measure for the different voxel positions may be applied to an image obtained by rendering or otherwise processing the first (or second) medical imaging data set representative of the inhalation (or exhalation phase). The normality or abnormality map be displayed on the display screen under control of the display control unit 16.

Figure 4A:
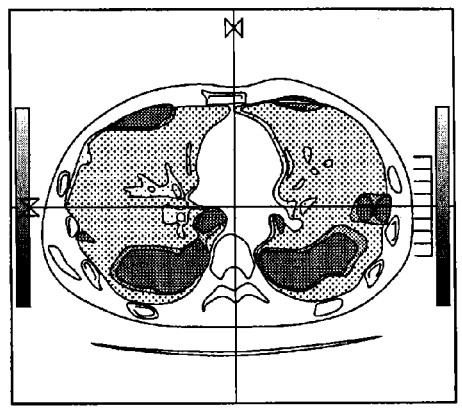
FIGS. 4 (FIG. 4a, FIG. 4b, FIG. 4c, and FIG. 4d) and 5 (FIG. 5a, FIG. 5b, FIG. 5c, and FIG. 5d) are slice images for patients with mild COPD and severe COPD respectively.
Figure 4B:
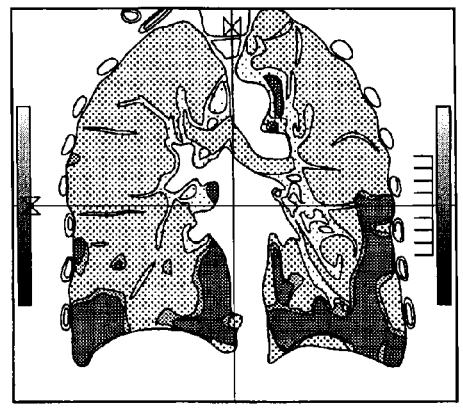
Figure 4C:
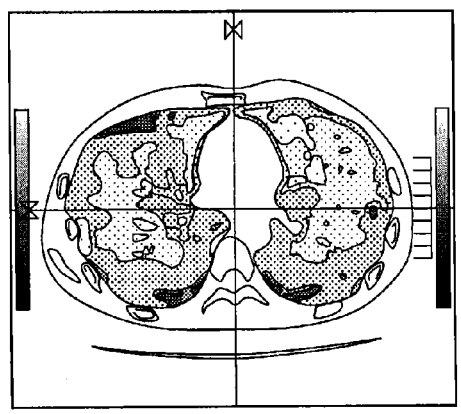
Figure 4D:
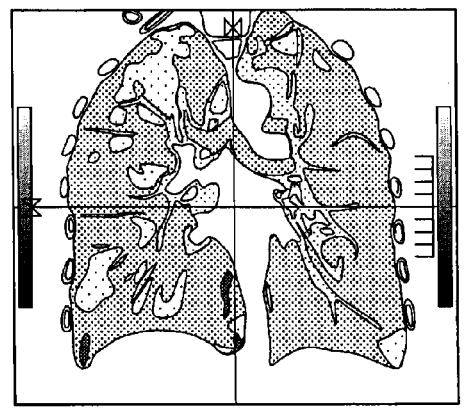

FIGS. 4c and 4d represent one example of a normality/abnormality map, made up of an axial slice image (FIG. 4c) and coronal slice image (FIG. 4d) obtained by processing the first image data set (e.g. an inhalation phase data set) for a patient with mild COPD. Each pixel in the image is colored or shaded dependent on the abnormality measure value for the voxel position corresponding to that pixel. For instance, in one example, pixels that are associated with positions where there is close to the expected local volume change for a normal patient may be colored green/cyan whereas pixels that are associated with positions where there are significant deviations from the expected local volume changes (for example, the lung volume changes less than expected for a normal patient) may be colored dark blue/purple.

Corresponding axial and coronal slice images in which each pixel in the image is colored or shaded dependent on the registration measure value (e.g. the log Jacobian scalar field value, representative of local volume change) for the voxel position corresponding to that pixel are shown in FIGS. 4a and 4b by way of comparison. It can be seen that there are dark shaded areas in FIGS. 4a and 4b corresponding to large volume change, but that corresponding areas in FIGS. 4c and 4d are no darker than the surrounding regions. That indicates that even though there are large local volume changes between inhalation and exhalation for those areas of the lungs, such large volume changes may be expected in normal lungs (as represented by the statistical atlas).

Figure 5A:
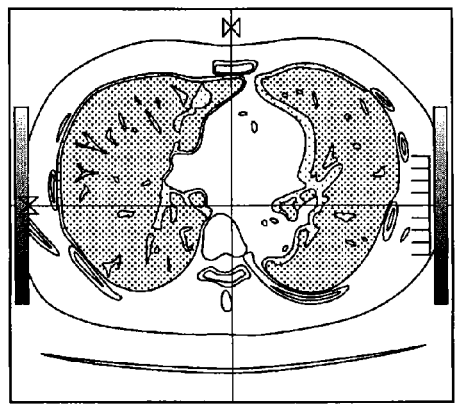
Figure 5B:
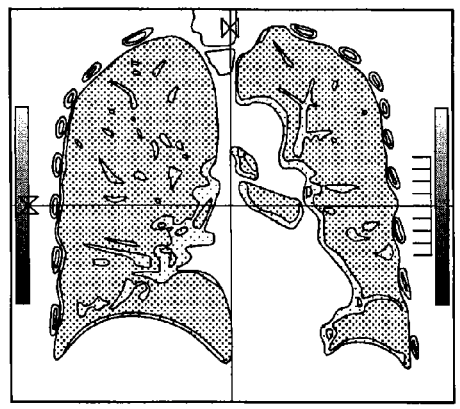
Figure 5C:
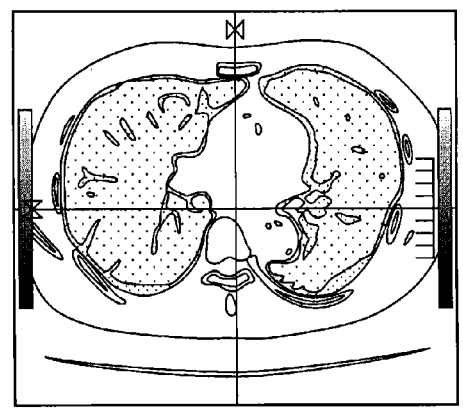
Figure 5D:
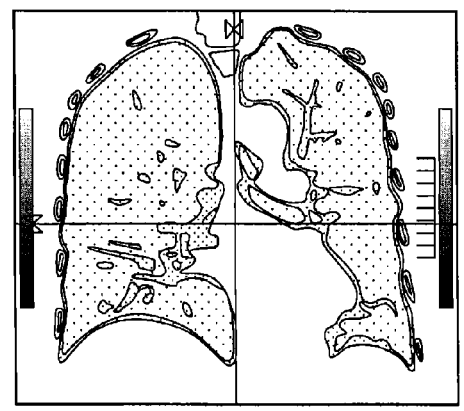

FIGS. 5a, 5b, 5c and 5d are axial slice images and coronal slice images that correspond to those of FIGS. 4a, 4b, 4c and 4d, with shading or coloring in FIGS. 5a and 5b dependent on registration measure values (e.g. log Jacobian values) and shading or coloring in FIGS. 5a and 5b dependent on abnormality measure values (e.g. statistical distance of the log Jacobian values from the centers of the distributions of log Jacobian values of the statistical atlas). However, FIGS. 5a, 5b, 5c and 5d are obtained from a patient with severe COPD rather than mild COPD. It can be seen that the dark shaded areas (indicating large local volume change) of FIGS. 4a and 4b are absent in FIGS. 5a and 5b, and that is indicative of an abnormality. Such abnormality is indicated in FIGS. 5c and 5d by suitable coloring or shading. In fact, most of the pixels in FIGS. 5c and 5d are similarly colored or shaded, indicating that most or all of the lungs that are the subject of FIGS. 5c and 5d are classified as being abnormal according to the method of the present embodiment.

Any suitable visual effect can be used to indicate abnormal (or, alternatively, normal) parts of a medical image obtained from the medical image data in alternative embodiments, for example any suitable visual effect can selectively be applied to parts of the image. For instance, any one or more of a shading, highlighting, blanking, fading, or application of a color may be used as the visual effect.

In the embodiment described above in relation to stage 44, the comparison of the registration measure values to the statistical atlas values is a one dimensional comparison in which, for each voxel position, the registration measure value (e.g. log Jacobian value) is compared to the distribution of registration measure values for that voxel position in the statistical atlas.

However, as described above, the scalar field in the described example is a two-dimensional scalar field that comprises both intensity values and registration measure values. In variants of the embodiment, the statistical atlas comprises or represents a joint distribution for each voxel position, in this example a joint distribution made up of distributions of both intensity values and registration values. The comparison at stage 44 in such variants is a comparison of both intensity and registration measure values to the joint distribution, and a statistical measure suitable for determining statistical distribution in relation to joint distributions can be used as the abnormality measure. For example, Mahalanobis distance may be used as, or in the determination of, the abnormality measure.

In alternative embodiments, the scalar field and the distributions of the statistical atlas may have any desired number of dimensions representing any desired number of parameters. For example, in some embodiments, in addition to the registration measure, an image texture parameter may be included as a parameter of the scalar field, and in the statistical atlas, as well as or instead of intensity.

In some embodiments various different statistical atlases may be stored in the data store, and the statistical atlas that is used may be selected by the evaluation unit in dependence on at least one property of the patient under investigation. For example, different statistical atlases may be stored that are obtained from reference subjects for different values of age range, weight range, range of body mass index (BMI), sex (male or female), smokers or non-smokers, or other properties. The atlas may then be selected in dependence, for example, on one or more of the age, weight, BMI, sex, or smoker/non-smoker status of the patient under investigation.

In the embodiment described in relation to FIGS. 1 to 3 the statistical atlas was pre-stored in data store 20. In variants of the embodiment, or in alternative embodiments, the statistical atlas is generated by system of FIG. 1 itself and stored in the data store 20. A process according to an embodiment for generating a statistical atlas is illustrated in overview in the flow chart of FIG. 6. As is described in more detail below, the process uses a database of normal (GOLD score of zero) inspire and expire lung volume data pairs to build the statistical atlas. For each pair, the scalar field of the desired metric (e.g. log of the Jacobian to give local volume change) is determined in a co-ordinate space of a template data set, and the scalar fields are used to build the statistical atlas.

Considering the process in more detail, at the first stage 70, previously stored pairs of reference medical image data sets are received by the receiving unit 24. For each pair, one of the sets of medical imaging data is CT scan data (referred to as inhalation data or inspire volume) representative of the chest cavity region of a subject and includes CT data representing the patient's lungs in an inhalation state (for example, when the patient was in the process of inhaling or had substantially fully inhaled). For each pair, the other of the sets of medical imaging data is also CT scan data (referred to as exhalation data or expire volume) representative of the chest cavity region of the same subject and includes CT data representing the patient's lungs during a subsequent exhalation state (for example, when the patient was in the process of exhaling or had substantially fully exhaled). In this embodiment, the atlas data set is intended to represent normal patients, without COPD, and each of the subjects has a GOLD score of zero.

At the next stage, the registration unit 26 registers each of the inhalation reference data sets together in a common co-ordinate system. The common co-ordinate system may be taken as being the co-ordinate system of one of the inhalation reference data sets, or may be any selected co-ordinate system. The registration unit transforms the inhalation reference data sets in accordance with the registrations so that corresponding anatomical features are represented in the same or similar positions in all of the transformed data sets.

The registration unit 26 then, for each voxel position, processes the intensity values for that voxel position from each of the transformed inhalation data sets to obtain an average intensity value for that voxel position and assigns that intensity value to the corresponding voxel of the template data set. Thus the template data set represents average intensity values obtained from the inhalation reference data sets.

At the next stage 74, for each pair of reference medical image data sets, the registration unit 26 registers the medical imaging set for the exhalation state to the medical imaging data set for the inhalation state to obtain registration data for that pair. In this embodiment the registration data is warp field data as described above in relation to stage 50 of FIG. 3.

At the next stage 76, for each pair of reference medical image data sets, and for each position, the evaluation unit 28 determines a registration measure value for that position and that pair. In this embodiment the registration measure value for each voxel and for each pair of datasets comprises, or is representative of, the log of the Jacobian of the registration warp field at that voxel position for the registration between the datasets of the pair. The log of the Jacobian is representative, for each voxel, of the local volume change between inhalation and exhalation as represented by the data sets of that pair.

At the next stage, the evaluation unit 28 generates a statistical atlas from the arrays of registration measure values obtained for the different pairs of reference data sets. For each voxel position, there will be a distribution of registration measure values obtained from the different pairs of reference data sets.

In some embodiments 28, the evaluation unit processes the registration measure values for each voxel position to determine at least one statistical parameter representative of the distribution of registration measure values at that position, and the statistical atlas then comprises an array of the determined statistical parameters. Any suitable statistical parameters may be used, for example one or more of mean, standard deviation, or any suitable distribution fit parameter. Alternatively or additionally, in some embodiments the statistical atlas comprises the arrays of registration measure values obtained for the different pairs of reference data sets, and the determination of statistical parameters, or the determination of where registration measure data for a particular patient lies with respect to the distribution, may be performed on-the-fly.

In some embodiments, the statistical atlas may be representative of joint distributions of registration measure values and values of at least one further parameter, for example image intensity or a texture parameter (e.g. intensity gradient).

Figure 6:
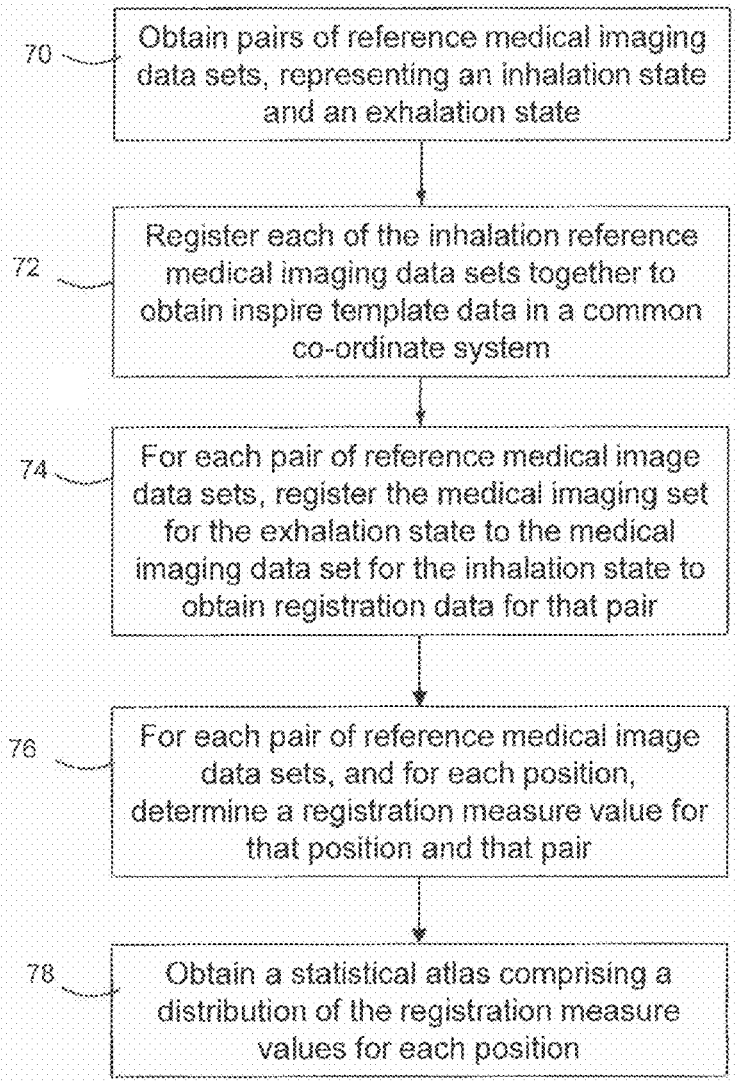
FIG. 6 is a flow chart representing in overview a process for generating a statistical atlas.

In the embodiment of FIG. 6, the registration processes performed by the registration unit 26 are non-rigid registration processes such as those described in relation to stages 50 and 56 of FIG. 3. However, any suitable alternative registration processes may be used in alternative embodiments.

The registration data in the particular example described above in relation to the embodiment of FIG. 2 comprises warp field data. In alternative embodiments the registration data may comprise any suitable type of data, for example any suitable type of vector or vector field data. The registration data does not necessarily comprise separate registration data entries for each voxel in some embodiments, and may represent a registration between the data sets in the co-ordinate space of the voxels without necessarily including data entries specifically associated with particular voxels. For example, the registration data may comprise a parametric representation of a vector field, and the interface identification unit may identify interfaces based on values of a spatially varying gradient, or higher order derivative, of the vector field. For example, if the spatially varying gradient, or higher order derivative of the vector field indicates that there is a region where the registration data changes sufficiently rapidly, for example substantially discontinuously, the interface identification unit may identify that region as an interface region.

Although embodiments have been described in which the registration data comprises or is representative of a log of a Jacobian of the registration warp field, any other suitable registration measures can be used in alternative embodiments. For example any suitable measure that is representative of local volume change between inhalation and exhalation phases may be used in some embodiments. Alternatively or additionally the registration data may comprise the magnitudes of the local displacements represented by the registration, for example Euclidean distances.

Although embodiments have been described in which each pair of medical imaging data sets comprises a data set obtaining during an inhalation phase and a data set obtained during an exhalation phase, in alternative embodiments both data sets may be obtained at different stages of an inhalation phase, or at different stages of an exhalation phase. Alternatively or additionally, a series of more than two medical imaging data sets may be used in some embodiments. Each of the data sets of the series may be registered to at least one other data set, for example a reference data set, to obtain at least one set of registration data in respect of each of the medical imaging data sets. Each of the sets of registration data can then be processed by the evaluation unit to determine values of a registration measure and to compare the registration measure values to a statistical atlas as described. The series of sets of medical imaging data may be obtained at different points on an inhalation-exhalation cycle. Alternatively or additionally the different data sets in the series of medical imaging data sets may be obtained during different scan procedures, for example on different days, and thus may for instance represent a longitudinal study of the patient.

Embodiments have been described in which values of the registration measure are compared to the statistical atlas. In alternative embodiments, values of one or more other parameters, for example parameters of the registered imaging data, instead of values of the registration measure are compared to the statistical atlas. In such embodiments the statistical atlas represents a distribution of the values of such other parameter or parameters. Examples of such other parameters include image intensity and/or image texture.

Embodiments have been described in relation to the processing of medical imaging data sets comprising CT data. Any suitable data sets may be used in alternative embodiments, for example magnetic resonance imaging (MRI) data sets, positron emission tomography (PET) data sets, or ultrasound data sets.

Medical imaging data can be in a variety of forms and can include any suitable data obtained from measurements by a medical imaging modality and/or any suitable data representative of one or more anatomical features. Medical imaging data may comprise any data that can be rendered, or otherwise processed, to obtain an image of at least part of a patient or other medical subject and/or any data that can be rendered, or otherwise processed, to obtain an image of one or more anatomical features. Volumetric medical imaging data may, for example, be in the form of an array of voxels. Such arrays of voxels may for example be representative of intensity, absorption or other parameter as a function of three-dimensional position, and may for example be obtained by suitable processing of measurement signals obtained by a medical imaging modality.

According to some embodiments, there may be provided a medical imaging method comprising a statistical atlas and a non-rigid registration algorithm in order to analyze and quantify lung disease from 3D volumetric data and generate a parametric normality map of the disease at the voxel level.

The lung disease may comprise COPD, and the 3D volumetric data may be inspiration and expiration CT scans. The 3D volumetric data may comprise two or more volumetric scans acquired at different inspiration levels. The method may comprise building the statistical atlas using the local volume change, calculated from the determinant of the Jacobian matrix of the registration warp field. The statistical atlas may be built using multiple metrics extracted from the warp field (e.g. local volume change, total volume change, etc.), image voxel data (e.g. intensity values, including derived metrics such as texture information) and patient information (e.g. smoking status, height, BMI, age, sex, etc.). The method may comprise outputting a normality map comprising a signed z-Score. The method may comprise outputting a normality map comprising a Mahalanobis distance.

According to some embodiments there is provided a medical imaging processing apparatus comprising a registration unit configured to register an inspiration image and an expiration image, an evaluation unit configured to calculate disease information based on a difference between pixel values of inspiration/expiration images and statistical atlas images, and a display control unit configured to display, on a display, the disease information based on the difference. The lung disease may be COPD, and the inspiration/expiration images may comprise 3D volumetric data.

It will be well understood by persons of ordinary skill of the art that embodiments may implement certain functionality by means of a computer program or computer programs having computer-readable instructions that are executable to perform the method of the embodiments. The computer program functionality could be implemented in hardware (for example by means of CPU). The embodiments may also be implemented by one or more ASICs (application specific integrated circuit) or by a mix of hardware or software.

Whilst particular units have been described herein, in alternative embodiments functionality of one or more of these units can be provided by a single unit, or functionality provided by a single unit can be provided by two or more units in combination. Reference to a single unit encompasses multiple components providing the functionality of that unit, whether or not such components are remote from one another, and reference to multiple units encompasses a single component providing the functionality of those units.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical imaging data processing apparatus comprising:
   processing circuitry configured to receive first medical imaging data that represents at least part of at least one lung of a subject at a first time, and second medical imaging data that represents the at least part of at least one lung of the subject at a second, later time, the first medical imaging data being representative of a first point of an inhalation-exhalation cycle and the second medical imaging data being representative of a second point of the inhalation-exhalation cycle, perform a registration procedure to obtain a registration between the first medical imaging data and the second medical imaging data, for each of a plurality of positions in the at least part of at least one lung, determine according to the registration a value of a registration measure at that position, the registration measure associated with a local volume change between the first point and the second point of the inhalation-exhalation cycle, and determine whether an abnormality is present by comparing the determined values of the registration measure to a statistical atlas comprising or representing a joint distribution of values of the registration measure and values of intensity or of an image texture parameter obtained in respect of a plurality of pairs of reference medical imaging data sets, each pair of the plurality of pairs of reference medical imaging data sets comprising medical image data representative of the first point and the second point of the inhalation-exhalation cycle, wherein the comparing of the determined values of the registration measure to the statistical atlas comprises, for each of the plurality of positions in the at least part of at least one lung, determining a measure of abnormality at that position, the measure of abnormality comprising a statistical distance that is representative of where the value of the registration measure and the value of intensity or of the image texture parameter fall on the join distribution.

2. The medical imaging data processing apparatus according to claim 1, wherein the processing circuitry is configured to obtain registration data representative of the registration between the first medical imaging data and the second medical imaging data, and process the registration data to determine, for each of the plurality of positions in the at least part of at least one lung, the determined value of the registration measure.

3. The medical imaging data processing apparatus according to claim 1, wherein the processing circuitry is configured to control a display to display an abnormality map representing the measures of the abnormality.

4. The medical imaging data processing apparatus according to claim 2, wherein the registration measure is representative of a size of a local deformation according to the registration.

5. The medical imaging data processing apparatus according to claim 2, wherein the registration data comprises a vector field, and the registration measure for a position comprises or is representative of a determinant of a Jacobian matrix of the vector field at that position.

6. The medical imaging data processing apparatus according to claim 1, wherein the statistical atlas comprises or represents a distribution of values that were obtained from a plurality of data sets obtained from measurements on a plurality of further subjects.

7. The medical imaging data processing apparatus according to claim 1, wherein the processing circuitry is configured to select the statistical atlas from a plurality of statistical atlases in dependence on a property of the subject.

8. The medical imaging data processing apparatus according to claim 7, wherein the property of the subject comprises at least one of age, sex, height, weight, body mass index (BMI), smoking status.

9. The medical imaging data processing apparatus according to claim 1, wherein the measure of abnormality comprises or represents at least one of a z-score, a Mahalanobis distance.

10. The medical imaging data processing apparatus according to claim 1, wherein the processing circuitry is configured to control a display to display an image representative of at least part of the subject, process at least one of the first medical imaging data or second medical imaging data to obtain the image for display, and for each of at least some positions in the image, apply a visual effect in dependence on the value of the measure of abnormality determined for that position.

11. The medical imaging data processing apparatus according to claim 1, wherein the visual effect comprises at least one of a shading, highlighting, blanking, fading, or application of a color.

12. The medical imaging data processing apparatus according to claim 2, wherein the registration data is representative of, for each a plurality of locations within the at least part of at least one lung, an offset of co-ordinates between the first medical imaging data and the second medical imaging data determined according to the registration procedure.

13. The medical imaging data processing apparatus according to claim 1, wherein the registration procedure comprises a non-rigid registration procedure.

14. The medical imaging data processing apparatus according to claim 1, wherein the registration data comprises at least one of vector field data or warp field data.

15. The medical imaging data processing apparatus according to claim 1, wherein the medical image data comprises at least one of computerized tomography (CT) data, magnetic resonance imaging (MRI) data, positron emission tomography (PET) data, or ultrasound data.

16. The medical imaging data processing apparatus according to claim 1, wherein the abnormality is associated with chronic obstructive pulmonary disease (COPD).

17. A medical imaging data processing method comprising:

receiving first medical imaging data that represents at least part of at least one lung of a subject at a first time, and second medical imaging data that represents the at least part of at least one lung of the subject at a second, later time, the first medical imaging data being representative of a first point of an inhalation-exhalation cycle and the second medical imaging data being representative of a second point of the inhalation-exhalation cycle;

performing a registration procedure to obtain a registration between the first medical imaging data and the second medical imaging data;

for each of the plurality of positions in the at least part of at least one lung, determining according to the registration a value of a registration measure at that position, the registration measure associated with a local volume change between the first point and the second point of the inhalation-exhalation cycle; and determining whether an abnormality is present by comparing the determined values of the registration measure to a statistical atlas comprising or representing a joint distribution of values of the registration measure and values of intensity or of an image texture parameter obtained in respect of a plurality of pairs of reference medical imaging data sets, each pair of the plurality of pairs of reference medical imaging data sets comprising medical image data representative of the first point and the second point of the inhalation-exhalation cycle, wherein the comparing of the determined values of the registration measure to the statistical atlas comprises, for each of the plurality of positions in the at least part of at least one lung, determining a measure of abnormality at that position, the measure of abnormality comprising a statistical distance that is representative of where the value of the registration measure and the value of intensity or of the image texture parameter fall on the joint distribution.

18. A non-transitory computer-readable medium storing instructions that are executable to perform a method comprising:

receiving first medical imaging data that represents at least part of at least one lung of a subject at a first time, and second medical imaging data that represents the at least part of at least one lung of the subject at a second, later time, the first medical imaging data being representative of a first point of an inhalation-exhalation cycle and the second medical imaging data being representative of a second point of the inhalation-exhalation cycle;

performing a registration procedure to obtain a registration between the first medical imaging data and the second medical imaging data;

for each of the plurality of positions in the at least part of at least one lung, determining according to the registration a value of a registration measure at that position, the registration measure associated with a local volume change between the first point and the second point of the inhalation-exhalation cycle; and determining whether an abnormality is present by comparing the determined values of the registration measure to a statistical atlas comprising or representing a joint distribution of values of the registration measure and values of intensity or of an image texture parameter obtained in respect of a plurality of pairs of reference medical imaging data sets, each pair of the plurality of pairs of reference medical imaging data sets comprising medical image data representative of the first point and the second point of the inhalation-exhalation cycle, wherein the comparing of the determined values of the registration measure to the statistical atlas comprises, for each of the plurality of positions in the at least part of at least one lung, determining a measure of abnormality at that position, the measure of abnormality comprising a statistical distance that is representative of where the value of the registration measure and the value of intensity or of the image texture parameter fall on the joint distribution.

19. The medical imaging data processing apparatus according to claim 7, wherein the processing circuitry is configured to select the statistical atlas from a plurality of statistical atlases in dependence on a property of the subject, the property of the subject comprising age, sex, height, weight, body mass index (BMI), and smoking status.

\* \* \* \* \*